United States Patent [19]
Day

[11] Patent Number: 5,380,522
[45] Date of Patent: Jan. 10, 1995

[54] METHOD FOR TREATMENT OF IRRITABLE BOWEL SYNDROME

[76] Inventor: Charles E. Day, 1224 Bear Creek Rd., Leitchfield, Ky. 42754

[21] Appl. No.: 928,509

[22] Filed: Aug. 11, 1992

[51] Int. Cl.⁶ ............... A61K 31/74; A01N 43/04
[52] U.S. Cl. ............... 424/78.08; 514/54; 514/57; 514/58; 514/59
[58] Field of Search ............ 514/54, 57, 58, 59; 424/78.08

[56] References Cited

U.S. PATENT DOCUMENTS

| | | | |
|---|---|---|---|
| 3,579,634 | 5/1971 | Brown | 514/57 |
| 3,627,872 | 12/1971 | Parkinson | 514/57 |
| 3,974,272 | 8/1976 | Pollie et al. | 424/78 |
| 4,172,120 | 10/1979 | Todd et al. | 424/44 |
| 4,303,638 | 12/1981 | Tayot et al. | 424/92 |
| 4,895,723 | 1/1990 | Amer et al. | 424/79 |
| 4,999,341 | 3/1991 | Ferro | 514/33 |
| 5,026,555 | 6/1991 | Killeen | 424/439 |
| 5,102,664 | 4/1992 | Day | 424/440 |
| 5,112,856 | 5/1992 | Gaginella et al. | 514/456 |
| 5,213,806 | 5/1993 | Ito et al. | 424/462 |

OTHER PUBLICATIONS

The Merck Manual of Diagnosis and Therapy, Fifteenth Edition (1987), pp. 796–811.
Official Gazette dated Jun. 1, 1993; Patent No. 5,216,002.
"Cholestyramine plus Pectin in Treatment of Patients with Familial Hypercholesterolemia", Atherosclerosis, 44 (1982) 379–383.

Primary Examiner—Douglas W. Robinson
Assistant Examiner—Deborah K. Ware
Attorney, Agent, or Firm—Gordon W. Hueschen

[57] ABSTRACT

A method of treating irritable bowel syndrome, including diarrhea, constipation, and pain aspects thereof, in a human patient, whereby the method involves the step of orally administering to the human patient an amount of an anion-binding polymer and a hydrophilic polymer, either simultaneously, concurrently, or in the form of a pharmaceutical composition wherein the anion-binding polymer and the hydrophilic polymer alleviate irritable bowel syndrome.

9 Claims, No Drawings

METHOD FOR TREATMENT OF IRRITABLE BOWEL SYNDROME

FIELD OF THE INVENTION

Method of treating and preventing irritable bowel syndrome employing combination therapy using an anion-binding polymer and a hydrophilic polymer. Pharmaceutical compositions, consisting essentially of an anion-binding polymer and a hydrophilic polymer, which are effective for treating and preventing the symptoms of irritable bowel syndrome.

BACKGROUND OF THE INVENTION AND PRIOR ART

This invention relates to a method and means for treating or preventing irritable bowel syndrome with a combination of polymeric substances or materials comprising as essential components an anion-binding polymer and a hydrophilic polymer. Irritable bowel syndrome is a complex of gastrointestinal symptoms manifested by abdominal pain and distention and by altered bowel habits. It is the most common symptom complex encountered by gastroenterologists and may account for 50% of outpatient gastroenterological complaints. There are no known organic causes for the disease, and it is frequently associated with stress and emotional disturbance. Irritable bowel syndrome occurs most frequently in the age group from 20 to 50 years old and occurs two to five times more frequently in females than in males. This painful disease is prevalent in approximately 20% of the adult population of the USA. The consequences of the disease can be socially debilitating and induce severe sexual dysfunction in many patients, especially females. Although not life threatening, irritable bowel syndrome (IBS) is a major health problem from the standpoint of decreased quality of life and reduction of productivity.

There is presently no effective treatment for irritable bowel syndrome (K. B. Klein, Controlled treatment trials in the irritable bowel syndrome: a critique, Gastroenterology 95: 232–241, 1988). Although largely ineffective, current treatment is multifactorial and consists of stress management, diet, and drugs, in that order. The patient is reassured that the disease is not life threatening and is advised to reduce or eliminate any controllable stress in his or her life. Relaxation exercises and biofeedback may be attempted to alter the psychogenic components of the illness. With respect to diet, the patient is advised to avoid any food to which he or she possesses a known sensitivity with respect to exacerbating the problem. A high fiber diet, either insoluble wheat bran or soluble psyllium, is almost routinely recommended, but with little if any positive benefit (Dietary fiber, food intolerance, and irritable bowel syndrome, Nutrition Reviews 48: 343–346, 1990).

Numerous drugs have been tried for the treatment of irritable bowel syndrome, but none has demonstrated sufficient efficacy to be of practical benefit to most patients. Psychoactive drugs, such as anxiolytics and antidepressants, even if effective for a given patient, have very limited, short-term utility because of the high potential for addiction to and abuse of these agents. Antispasmodics and various antidiarrheal preparations have been used but, even if they are effective, long-term treatment is precluded by problems such as development of tolerance, toxicity, or abuse potential. Several excellent reviews examine in detail the symptomology, diagnosis, and treatment of irritable bowel syndrome. These include: W. L. Hasler and C. Owyang, Irritable bowel syndrome, In: Textbook of Gastroenterology, Ed. by T. Yamada, J. B. Lippincott Company, Philadelphia, Pa., 1696–1714 (1991); M. M. Schuster, Irritable bowel syndrome, In: Gastrointestinal Disease, Pathophysiology Diagnosis and Management, Fourth Edition, Ed. by M. H. Sleisenger, J. S. Fordtran, W. B. Saunders Company, Philadelphia, Pa., 1402–1418 (1989); and W. S. Haubrich, Irritable bowel syndrome, Gastroenterology, Fourth Edition, Ed. by J. E. Berk, W. B. Saunders Company, Philadelphia, Pa., 2425–2444 (1985).

Numerous patents have claimed activities of various types represented as being effective for relieving irritable bowel syndrome symptoms. For the most part they relate to substances which possess spasmolytic activity and thereby decrease intestinal motility. U.S. Pat. Nos. 4,611,011, 4,701,457, and 4,745,131 disclose a series of amidinoureas which reduce intestinal motility and are useful for treating irritable bowel syndrome. 1-Azabicyclo[2.2.2]octan-3-yl-2-aryl-3-azacyclo-2-hydroxypropionates and their quaternary salts, which possess antispasmodic activity and are useful for treating irritable bowel syndrome, are disclosed in U.S. Pat. No. 4,843,074. Calcium channel antagonists exhibit muscle relaxing and antispasmodic activities. A series of substituted imidazolyl-alkyl-piperazine and diazepine derivatives, disclosed in U.S. Pat. No. 5,043,447, are calcium channel antagonists and may be useful as antispasmodics for treating irritable bowel syndrome. 2-Aminomethylalkynylalkyl-1,3-dithiane derivatives with calcium-channel blocking activity and potentially similar uses are disclosed in U.S. Pat. No. 4,877,779. A series of triazinone derivatives with spasmolytic activity for treating irritable bowel syndrome are disclosed in U.S. Pat. No. 4,562,188.

In addition to antispasmodic agents, compounds with other activities have been disclosed which may relieve the symptoms of irritable bowel syndrome. U.S. Pat. No. 4,239,768 discloses a series of arylimidazolidinylidene ureas which decrease the sensitivity of the bowel to distension and thereby relieve irritable bowel symptoms. U.S. Pat. No. 4,970,207 discloses a series of benzodiazepine derivatives which are cholecystokinin antagonists and which may be useful for a large number of medical indications which include irritable bowel syndrome.

Since diarrhea is one frequent component of irritable bowel symptomatology, anti-diarrheal agents have been used to treat this disease. Unfortunately, such agents tend to exacerbate the constipatory phase of the disease and are, therefore, of little practical, long-term benefit.

Calcium polycarbophil is a hydrophilic polymeric substance which is sold as an over-the-counter preparation for the relief of irritable bowel syndrome symptoms. A low degree of effectiveness has precluded widespread use of this material by patients suffering from irritable bowel symptoms.

In spite of the many treatments and inventions devised to relieve or prevent irritable bowel syndrome, the unfortunate fact is that presently no suitable long term, safe and efficacious treatment or preventative is available for this troublesome and widespread disease.

To the best of my knowledge, no such combination therapy has been suggested for the treatment of irritable bowel syndrome. Moreover, the only known references which even come close are U.S. Pat. No. 5,102,664, by the present applicant, in which compositions for the control of hypercholesterolemia are disclosed, comprising cholestyramine and pectin together with a seedy fibrous fruit and other materials for effecting the oral acceptability of gritty drugs, most of the components of which composition are unnecessary according to the present invention, and the prior art cited in that patent, as well as a publication by Schwandt, et al. entitled "CHOLESTYRAMINE PLUS PECTIN IN TREATMENT OF PATIENTS WITH FAMILIAL HYPERCHOLESTEROLEMIA", appearing in Atherosclerosis 44, 379-383 (1982), in which granular pectin and cholestyramine were individually administered to patients having hypercholesterolemia in an amount of 28 grams per day for the entirely different purpose of that study.

Accordingly, to the best of my knowledge, no combination of the essential polymers employed according to the method of the invention has ever been employed in any way for the treatment or prevention of irritable bowel syndrome, nor has any pharmaceutical composition consisting essentially of dry powdered admixtures thereof been made available for such purpose.

OBJECTS OF THE INVENTION

It is an object of the present invention to provide novel pharmaceutical compositions which are useful, when orally administered, for the effective treatment or prevention of irritable bowel syndrome, including the component diarrhea and constipational and pain aspects thereof, in a human patient. It is a further object of the present invention to provide a method-of-treating irritable bowel syndrome, including the aforesaid component aspects thereof, by the oral administration of such a pharmaceutical composition, consisting essentially of an anion-binding polymer and a hydrophilic polymer. Another object of the invention is to provide such a composition and method wherein the anion-binding polymer is cholestyramine or a pharmaceutically-acceptable colestipol salt, which are preferred among numerous other anion-binding polymers which are useful for the aforesaid purpose. A further object of the invention is the provision of such a pharmaceutical composition and method involving pectin as a preferred hydrophilic polymer, among numerous others which are suitable for the aforesaid purpose. A still further object of the invention is the provision of such a method wherein the anion-binding polymer and the hydrophilic polymer are orally administered simultaneously or concurrently, although the preferred manner of administration is in the form of an orally-acceptable pharmaceutical composition consisting essentially of the anion-binding polymer and the hydrophilic polymer, particularly in the form of a dry powder admixture thereof, which can be readily dispersed or suspended in a minor amount of fluid, e.g., water, just prior to oral ingestion. Still a further object of the invention is the provision of a pharmaceutical composition and method for the treatment and prevention of irritable bowel syndrome which employs a polymer which is both an anion-binding polymer and a hydrophilic polymer, such as chitosan, for the aforesaid purpose. Additional objects of the invention will become apparent hereinafter and still others will be obvious to one skilled in the art to which this invention pertains.

SUMMARY OF THE INVENTION

The invention, then, comprises the following, inter alia, singly or in combination:

A method of treating or preventing irritable bowel syndrome, including diarrhea, constipation, and pain aspects thereof, in a human patient, consisting essentially of the step of orally administering to the said human patient an amount of an anion-binding polymer and a hydrophilic polymer, either simultaneously, concurrently, or in the form of a pharmaceutical composition consisting essentially of the anion-binding polymer and the hydrophilic polymer, or consisting essentially of a polymer which is both an anion-binding polymer and a hydrophilic polymer, which is effective for alleviation or prevention of the said irritable bowel syndrome; such a method wherein the weight ratio of the anion-binding polymer to the hydrophilic polymer is between about 2:1 and about 1:2; such a method wherein the total amount of polymer per dose is between about 1 g and 24 g; such a method wherein the weight ratio of the anion-binding polymer to the hydrophilic polymer is between about 2:1 and about 1:2 and wherein the total amount of polymer per dose is between about 1 g and about 24 g; such a method wherein the anion-binding polymer is cholestyramine and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a method wherein the anion-binding polymer is a colestipol pharmaceutically-acceptable acid addition salt and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a method wherein the anion-binding polymer is MCI-196 and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a method wherein the anion-binding polymer is diethyl-aminoethyl dextran and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a method wherein the anion-binding and hydrophilic characteristics are combined in a single polymer; such a method wherein the polymer is chitosan; such a method wherein the anion-binding polymer is cholestyramine or a colestipol salt and wherein the hydrophilic polymer is pectin.

Moreover, an orally-ingestible pharmaceutical composition useful for the effective oral treatment or prevention of irritable bowel syndrome, including diarrhea, constipation, and pain aspects thereof, in a human patient, consisting essentially of a dry powdered admixture of an amount of an anion-binding polymer and a hydrophilic polymer, or a polymer which is both an anion-binding polymer and a hydrophilic polymer, optionally together with a pharmaceutically-acceptable diluent or carrier, which can conveniently be admixed with and suspended in a minor amount of fluid just prior to oral ingestion, which is effective for such purpose; such a pharmaceutical composition wherein the weight ratio of the anion-binding polymer to the hydrophilic polymer is between about 2:1 and about 1:2; such a
  pharmaceutical composition wherein the total amount of polymer per dose of the composition is adapted to be between about 1 g and 24 g; such a
  pharmaceutical composition wherein the weight ratio of the anion-binding polymer to the hydrophilic polymer is between about 2:1 and about 1:2 and wherein the total amount of polymer per dose of the composition is adapted to be between about 1 g and about 24 g; such a
  pharmaceutical composition wherein the anion-binding polymer is cholestyramine and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a
  pharmaceutical composition wherein the anion-binding polymer is a colestipol pharmaceutically-acceptable acid addition salt and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a
  pharmaceutical composition wherein the anion-binding polymer is MCI-196 and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a
  pharmaceutical composition wherein the anion-binding polymer is diethylaminoethyl dextran and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil; such a
  pharmaceutical composition wherein the anion-binding and hydrophilic characteristics are combined in a single polymer; such a
  pharmaceutical composition wherein the polymer is chitosan; and finally, such a
  pharmaceutical composition wherein the anion-binding polymer is cholestyramine or a colestipol salt and wherein the hydrophilic polymer is pectin.

GENERAL DESCRIPTION AND NATURE OF THE INVENTION

Bile acid sequestrants are high-molecular weight cationic polymers which bind bile acid anions in the gastrointestinal tract and are useful for reducing serum cholesterol levels. These anion-binding polymers act non-systemically and are very safe for long term use since they are neither degraded nor absorbed from the gastrointestinal tract. Constipation is a frequent side effect of bile acid sequestrant administration (L. M. Hagerman and C. E. Day, Chemistry and pharmacology of bile salt sequestrants, In: Antilipidemic Drugs: Medicinal, Chemical and Biochemical Aspects, Ed. by D. T. Witiak, H. A. I. Newman and D. R. Feller, Elsevier, N.Y., 197–223 (1991).) Therefore, bile acid sequestrants alone are not useful agents for treating the constellation of symptoms associated with irritable bowel syndrome.

Pectin is a hydrophilic polymer found in virtually all plants. A combination of pectin and kaolin has been used for decades as a popular anti-diarrheal treatment. But, as with other anti-diarrheal preparations, a kaolin plus pectin combination is not useful for long-term management of irritable bowel syndrome because of its constipatory effects.

It has now been unexpectedly and fortuitously discovered that a combination of an anion-binding polymer and a hydrophilic polymer can be used for the treatment and prevention of the symptoms of irritable bowel syndrome. The initial discovery involved a combination of the bile acid sequestrant cholestyramine and the hydrophilic polymer pectin. Subsequent to the initial discovery, it was demonstrated that combinations of other anion-binding polymers with other hydrophilic polymers are also effective for treating and preventing irritable bowel symptoms. It is only the combination of anion-binding polymer and hydrophilic polymer which is effective in preventing and relieving symptoms of this disease.

Anion-binding polymers which can be used effectively in this combination include, but are not limited to, cholestyramine, colestipol hydrochloride, diethylamino-ethyldextran, chitosan, MCI-196, and divistyramine. Hydrophilic polymers which can be used effectively in this combination include, but are not limited to, pectin, guar gum, psyllium hydrophilic colloid, calcium polycarbophil, alginic acid, xanthan gum, carrageenan, locust bean gum, oat bran beta-glucan, glucomannan, tapioca, cellulose gums, and agar. Of course this invention is not limited to combinations of the specific substances cited above inasmuch as, based upon the disclosure of this application, anyone skilled in the art can readily conceive of other specific combinations of anion-binding and hydrophilic polymers which will be effective for treating or preventing irritable bowel syndrome.

DETAILED DESCRIPTION OF THE INVENTION

The following Examples are given to illustrate the method and some combination formulations or compositions of the present invention, but are not to be construed as limiting:

EXAMPLE ONE

The patient was a white male who, in his early forties, was first presented with the gastrointestinal complaints of alternating bouts of diarrhea, constipation, abdominal pain, and irregular bowel habits. On the basis of negative gastrointestinal radiographic and sigmoidoscopic evidence and the absence of other demonstratable organic disease, a diagnosis of irritable bowel syndrome was made. For the next few years the symptoms became progressively worse in spite of recommended changes in dietary habits and the use of numerous anti-diarrheal preparations. Over a period of a few years, the patient tried as single preparations, each time in succession, the following medicaments: loperamide, attapulgite, psyllium hydrocolloid, oat bran, wheat bran, paregoric, pectin, pectin plus kaolin, cholestyramine, colestipol hydrochloride, guar gum, calcium polycarbophil, diphenoxylate hydrochloride plus attopine sulfate, and many other over-the-counter and home remedies for diarrhea. None of these treatments proved effective for the patient, and his symptoms grew progressively worse.

While researching on a project to improve the taste of cholesterol-lowering products, the patient found it necessary to routinely taste numerous preparations to evaluate his progress on the project. After sampling several times one particular batch which did not taste particularly good, he noted that his irritable bowel symptoms disappeared for the next two days. The said preparation was essentially a mixture of cholestyramine and apple pectin in a weight ratio of 2:1, preferably suspended in a few ounces of water just before oral administration. On a basis of this unexpected observation, the patient then consumed prior to breakfast once daily for a period of one month a preparation of cholestyramine and pectin consisting of 4 g cholestyramine, 2 g pectin, and assorted flavoring and/or sweetening agents. During the period of cholestyramine plus pectin administration, all irritable bowel symptoms virtually disappeared. Frequency of abdominal pain and diarrhea decreased from an average of four times daily to only one single occurrence in two weeks, and no constipation occurred throughout the treatment period. After cessation of treatment with cholestyramine plus pectin, irritable bowel symptoms returned at their previous normal frequency within two days.

EXAMPLE TWO

After the initial successful results described in Example One, the patient tested other combinations of bile acid anion-binding polymers and hydrophilic polymers for their efficacy on irritable bowel syndrome symptoms. Five grams of dry powdered Colestid ® (colestipol hydrochloride) were mixed with 5 g of SureJel ® (a dried and powdered commercial preparation of dextrose and citrus pectin used for making jellies) and suspended in a few ounces of cold water. This mixture was consumed once daily prior to breakfast for a period of one month. Irritable bowel symptoms were eliminated with this combination and returned within two days after treatment ceased.

EXAMPLE THREE

Five grams of dried and powdered Colestid ® were mixed with 5 g of dried and powdered BioGuar ® (guar gum) and suspended in a few ounces of cold water. This mixture was consumed once daily prior to breakfast by the patient for a period of one month. Irritable bowel symptoms were prevented and controlled by this mixture during the period of treatment.

EXAMPLE FOUR

Five grams of dried and powdered Questran ® Light (cholestyramine plus flavors and sweeteners) were mixed with 5 g of dried and powdered JelEase ® (mixture of dextrose and fruit pectin used for making jelly) and suspended in a few ounces of cold water. This mixture was consumed once daily prior to breakfast by the patient for a period of twelve months. Irritable bowel symptoms were markedly reduced, comparable to what was observed in Example One, throughout this treatment period. Symptoms returned within a few days after cessation of treatment.

EXAMPLE FIVE

Five grams of dried and powdered Questran ® Light were mixed with 5 g of dried and powdered Equalactin ® (calcium polycarbophil plus flavoring and sweetening agents) and suspended in a few ounces of cold water. This mixture was consumed once daily prior to breakfast by the patient for one week. Irritable bowel symptoms were prevented and totally absent during the treatment period but returned after cessation of treatment.

EXAMPLE SIX

Five grams of dried and powdered Questran ® Light were mixed with 5 g of dried and powdered sugar-free Metamucil ® (psyllium hydrocolloid plus flavoring and sweetening agents) and suspended in a few ounces of cold water. This mixture was consumed by the patient once daily prior to breakfast for a period of one week. Irritable bowel symptoms were reduced by approximately one half, but not completely eliminated by this treatment.

ADDITIONAL EXAMPLES

In accord with the foregoing examples, the following combinations of anion-binding polymer and hydrophilic polymer were administered orally to a patient in the manner of the foregoing examples, the two essential active ingredients of the invention being administered either simultaneously or concurrently or, as previously indicated, preferably in the form of a pharmaceutical composition consisting essentially of the anion-binding polymer and the hydrophilic polymer, and preferably in the form of a dry powder admixture which may be conveniently dispersed or suspended in a few ounces of fluid, e.g., water, just prior to oral ingestion to facilitate administration and eliminate excessive swelling in the mouth which might interfere with patient compliance. The dosages employed ranged from 1 g per dose to 24 g per dose, the relative weight proportions of the anion-binding polymer and the hydrophilic polymer being between 2:1 and 1:2, and the amount of each per dose advantageously being between ½ g of each to 12 g of each of the active ingredients, preferably between about 1 and 6 g of each of the active ingredients per unit dose. The dosage regimen is usually one dose per day, advantageously prior to breakfast, but other dosage regimens, such as twice a day prior to both breakfast and bedtime or in other equal or unequal dosages spaced throughout the day, for example three times daily, may be employed, the unit dosages being determined by the number of oral applications involved per day. In each case, the treatment is found to be effective in the prevention, amelioration, alleviation, or elimination of irritable bowel symptoms, including the usually attendant diarrhea, constipation, and pain.

As already stated, the following combinations of active ingredients may be administered concurrently or simultaneously, but are preferably administered in the form of a pharmaceutical composition consisting essentially of the two active ingredients, namely, the anion-binding polymer and the hydrophilic polymer. Naturally, lower dosages are less effective than the higher dosages, although higher dosages present the usual problem of adequate patient compliance, especially when the upper ranges result in an objection due to the bulk or mass involved.

Representative combinations employed, and the combinations when embodied in the form of a pharmaceutical composition consisting essentially thereof, are as follows: cholestyramine plus pectin, guar gum, psyllium hydrophilic colloid, locust bean gum, alginic acid, cellulose gum, carrageenan, oat bran beta-glucan, xanthan gum, or methylcellulose.

Colestipol pharmaceutically-acceptable salt, e.g., the hydrochloride, plus pectin, guar gum, psyllium hydrophilic colloid, locust bean gum, cellulose gum, alginic acid, carrageenan, oat bran beta-glucan, xanthan gum, or methylcellulose.

The anion-binding polymer MCI-196 (Mitsubishi Chemical Industries designation—bile acid sequestrant reportedly licensed to Bristol-Myers-Squibb in the USA) and pectin, guar gum, psyllium hydrophilic colloid, locust bean gum, cellulose gum, alginic acid, carrageenan, oat bran beta-glucan, xanthan gum, or methylcellulose.

Diethylaminoethyl dextran and pectin, guar gum, psyllium hydrophilic colloid, locust bean gum, cellulose gum, alginic acid, carrageenan, oat bran beta-glucan, xanthan gum, or methylcellulose.

Additional effective combinations and pharmaceutical compositions consist essentially of cholestyramine and polycarbophil, colestipol hydrochloride and polycarbophil, MCI-196 and polycarbophil, and diethylaminoethyl dextran and polycarbophil.

In further trials, the compound employed is a polymer exhibiting both anion-binding characteristics and hydrophilic characteristics, namely, chitosan, which is deacetylated chitin. This polymeric material is orally administered either alone or, as usual in any case, in combination with a suitable pharmaceutically-acceptable excipient or diluent, such as lactose, flavoring, or the like, or if desired in combination (as the anion-binding polymer) together with another hydrophilic polymer such as pectin, or in combination (as the hydrophilic polymer) together with another anion-binding polymer such as cholestyramine, and the results are found to be outstanding. The amount of chitosan employed in such method or in such pharmaceutical compositions may be between about 0.5 g and 12 g, preferably between about 1 and 6 g, when used in combination, or 1 g to 24 g, preferably between about 2 and 12 g, when used alone.

It is therefore seen that the present invention provides a novel and effective composition and method of treating and preventing the symptoms of irritable bowel syndrome comprising a combination consisting essentially of an anion-binding polymer and a hydrophilic polymer, either simultaneously or concurrently administered, or admixed together, in effective amounts, and in any case orally administered, all having the unpredictable and highly advantageous characteristics and effects as more fully set forth in the foregoing, and whereby all the objectives of the present invention are attained.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A method of treating irritable bowel syndrome, including diarrhea, constipation, and pain aspects or symptoms thereof, in a human patient, consisting essentially of the step of orally administering to the said human patient an amount of an anion-binding polymer and a hydrophilic polymer, either simultaneously, concurrently, or in the form of a pharmaceutical composition consisting essentially of the anion-binding polymer and the hydrophilic polymer which is effective for alleviation of said irritable bowel syndrome.

2. The method of claim 1, wherein the weight ratio of the anion-binding polymer to the hydrophilic polymer is between about 2:1 and about 1:2.

3. The method of claim 1, wherein the total amount of both polymers per dose is between about 1 g and 24 g.

4. The method of claim 1, wherein the weight ratio of the anion-binding polymer to the hydrophilic polymer is between about 2:1 and about 1:2 and wherein the total amount of both polymers per dose is between about 1 g and about 24 g.

5. The method of claim 4, wherein the anion-binding polymer is cholestyramine and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil.

6. The method of claim 4, wherein the anion-binding polymer is a colestipol pharmaceutically-acceptable acid addition salt and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil.

7. The method of claim 4, wherein the anion-binding polymer is MCI-196 and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil.

8. The method of claim 4, wherein the anion-binding polymer is diethylaminoethyl dextran and the hydrophilic polymer is selected from the group consisting of pectin, guar gum, psyllium hydrophilic colloid, locust bean gum, alginic acid, cellulose gum, carrageenan, oat bran beta-glucan, xanthan gum, methylcellulose, and polycarbophil.

9. The method of claim 4, wherein the anion-binding polymer is cholestyramine or a colestipol salt and wherein the hydrophilic polymer is pectin.

* * * * *